United States Patent [19]
McKenna et al.

[11] Patent Number: 6,147,244
[45] Date of Patent: Nov. 14, 2000

[54] PREPARATIONS OF THIOPHOSPHITES AND THIOPHOSPHONATES

[75] Inventors: Charles E. McKenna, Pacific Palisades, Calif.; Zengmin Li, New York, N.Y.

[73] Assignee: University of Southern California, Los Angeles, Calif.

[21] Appl. No.: 09/304,252

[22] Filed: May 3, 1999

[51] Int. Cl.$^7$ ........................................ C07F 9/06
[52] U.S. Cl. ......................... 558/132; 558/207; 558/214
[58] Field of Search ............................ 558/70, 132, 207, 558/214

[56] References Cited

U.S. PATENT DOCUMENTS

| | | | |
|---|---|---|---|
| 4,466,895 | 8/1984 | Schroeck et al. | |
| 5,072,032 | 12/1991 | McKenna | 562/9 |
| 5,183,812 | 2/1993 | McKenna | 514/120 |

FOREIGN PATENT DOCUMENTS 219 198  2/1985  German Dem. Rep. .

OTHER PUBLICATIONS

CA:106:148259 abs of Chem Tech by Zimmermann et al 38(4) pp. 169–72, 1986.

CA:107:7017 abs of J Chem Soc Perkin Trans 1 (12) pp. 2081–2090 by Dingwall, 1986.

CA:110:114931: abs of Zh. Obshch. Khim. 57(12) pp. 2716–2719 by Chepakova, 1987.

L. Gerard, et al. "Pharmacology and Clinical Use of Foscarnet", Elsevier Science B.V., 1995, pp. 209–217.

C.E. McKenna, et al. "Functional Selectivity in Phosphonate Ester Dealkylation with Bromotrimethysilane", J.C.S. Chem. Comm., 1979, p. 739.

F. Noormohamed, et al. "Pharmacokinetics and Absolte Bioavailabilty of Oral Foscarnet in Human Immunodeficiency Virus–Seropositive Patients", Dept. of Clinical Pharmacology and Therapeutics; Imperial College School of Medicine, HIV Unit; St. Stephen's Clinic; Chelsea and Westminster Hospital, London, U.K.; and Astra, Inc., Westborough, MA., Revised Jul. 18, 1997, pp. 293–297.

*Primary Examiner*—Jean F Vollano
*Attorney, Agent, or Firm*—Fulbright & Jaworski L.L.P.

[57] ABSTRACT

Improved methods for converting phosphite or phosphonate esters into corresponding thiophosphites or thiophosphonates and for synthesizing specific thiophosphite and thiophosphonate compounds so produced are disclosed and claimed. The methods start from phosphite diesters using $P_4S_{10}$ as the thionation reagent. The reaction mixture is refluxed until the reaction is complete and may be followed by separation and chloroformate ester phosphonation steps to produce pure thiophosphonocarboxylate triesters. Alternatively, these esters may be prepared directly by action of $P_4S_{10}$ on the corresponding phosphonocarboxylate esters. The former method was used to prepare dimethyl thiophosphite and thence trimethyl thiophosphonoformate, a key intermediate in synthesis of salts of thiophosphonoformic acid, which have anti-viral properties.

10 Claims, 2 Drawing Sheets

PREPARATIONS OF THIOPHOSPHITES AND THIOPHOSPHONATES

FIELD OF INVENTION

The present invention relates to the general field of phosphorus chemistry, and is particularly directed to improved methods for large scale production of thioanalogues of phosphonoformic acid (PFA), and to the conversion of phosphonates into thiophosphonates in general, and to the conversion of phosphites into their corresponding thiophosphite derivatives.

BACKGROUND

Phosphonates play a significant role in the fields of chemistry, biology and medicine. Moreover, phosphonate analogues have been shown to possess biologically or economically important properties as pesticides, insecticides, herbicides, enzyme inhibitors and receptor antagonists. Thus, these compounds have become increasingly important in the fields of agriculture and medicine.

Due to their widespread applications, considerable activity has been devoted to developing convenient methods for synthesis of phosphonates or related compounds. However, the discovery of novel phosphonates or related compounds and new methods for synthesizing them in large quantities in a simple, fast, efficient manner with high yields remains of interest. Further, it would be advantageous to be able to synthesize these compounds in a cost-effective manner.

α-Phosphonocarboxylate compounds, a class of phosphonate derivatives, are endowed with special physical, chemical and biological properties. Various uses of these derivatives, arising from the proximity of the carboxyl and phosphonyl groups, range from metal chelation to the manifestation of biological activity. For example, phosphonocarboxylate compounds can be used as inhibitors of enzymes which catalyze reactions of biological phosphate derivatives, such as nucleoside 5'-triphosphates and oligonucleotides.

One phosphonocarboxylate derivative, phosphonoformic acid (PFA), has been found to possess antiviral properties, and in the form of its trisodium salt (foscarnet), PFA has a role in the treatment of some viral diseases, such as Cytomegalovirus (CMV) retinitis in AIDS. PFA was also shown to inhibit HIV-1, the retrovirus generally believed to cause Acquired Immune Deficiency Syndrome (AIDS).

A sulfur analogue of PFA, thiophosphonoformic acid (TPFA) in the form of a trisodium salt (Thiovir®), was found effective against HIV, the AIDS virus, in previous U.S. patents (U.S. Pat. Nos. 5,072,032 and 5,183,812, the disclosures of which are hereby incorporated by reference in their entirety, including cited references). A novel, simple synthesis of Thiovir® was reported in these patents, which teach that Thiovir® can be prepared from trimethyl phosphonoformate via a trimethyl thiophosphonoformate intermediate. The intermediate can be formed by the action of Lawesson's Reagent (LR); [2,4-bis(4-methoxyphenyl)-1,3-dithia-2,4-diphosphetane-2,4-disulfide] on trimethyl phosphonoformate. Thiovir® has been completely characterized by elemental analysis, $^{31}P$, $^{13}C$ and $^{1}H$ NMR, UV, IR and X-ray crystallographic analysis.

Thiovir® and related compounds are particularly well suited for use as effective antiviral agents. Thiovir® showed unexpectedly high antiviral activity against HIV compared to its DNA polymerase inhibiting activity. Biochemical assays showed that Thiovir® selectively inhibited isolated HIV reverse transcriptase (RT) in vitro with an $IC_{50}$ of about 1 μM, but foscarnet was more inhibitory to human DNA polymerases. Both Thiovir® and foscarnet can be non-toxic to cultured H9 cells at effective antiviral doses, and showed similar inhibition dose dependencies based on a p24 antigen capture assay. Moreover, Thiovir® also exhibited antiviral activity against CMV-infected cells in culture.

Unfortunately, there are disadvantages associated with the previously developed methods and reagents used to make Thiovir® compounds. For example, the prior art method of synthesizing Thiovir® typically involves using Lawesson's reagent as a thionating reagent, which is expensive. Consequently, the cost of using this method on a large scale may be excessive.

In view of the apparent utility of these compounds, developing less expensive, and equally simple methods to produce triesters of thiophosphonoformic acid is desirable. Accordingly, it is a principal object of the present invention to disclose a new, improved method for the effective production of large quantities of trimethyl thiophosphonoformate, which is the most important intermediate in the synthesis of Thiovir®. Moreover, the costs associated with producing Thiovir®, using the methods and intermediates of the present invention, should be significantly less than those of previously reported methods.

As those skilled in the art would appreciate, it is also an object of the present invention to disclose novel, improved methods for converting the general class of phosphites and phosphonates into their corresponding thio derivatives in a simple and economical manner.

BRIEF DESCRIPTION OF THE DRAWINGS

These and other features, aspects, and advantages of the present invention will become better understood with regard to the following description, appended claims, and accompanying drawings where:

SUMMARY

Figure 1A:
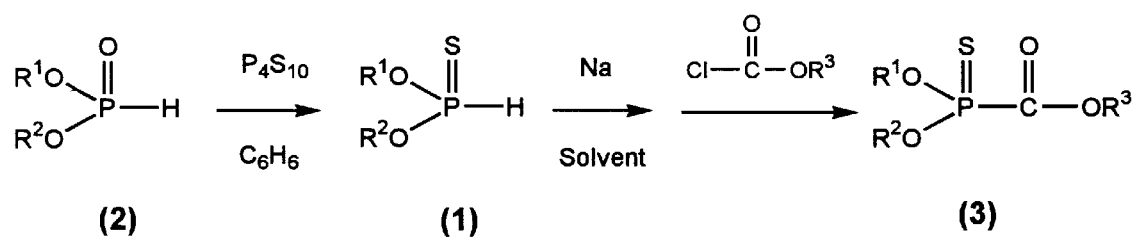
FIG. 1A schematically shows thionation by phosphorus pentasulfide ($P_4S_{10}$) of a phosphite compound (2) to give a thiophosphite compound (1), and the susbsequent phosphonation of a monoester of chloroformic acid, by the sodium salt of (1), to give a thiophosphonoformate triester (3)

Generally stated, the present invention accomplishes the above-described objectives by providing improved methods for converting phosphite esters, or phosphonate esters (such as trimethyl phosphonoformate), into thiophosphonate analogues (such as trimethyl TPFA) in high product yields in a cost-effective manner. Still further, the present invention provides improved methods for converting phosphite or phosphonate esters into corresponding thiophosphites or thiophosphonates, respectively, and for synthesizing specific thiophosphite and thiophosphonate compounds.

Furthermore, the methods of the present invention have wide applicability in selectively producing large quantities of thiophosphites and thiophosphonate compounds for the economic production of a wide variety of compounds including insecticides incorporating thiophosphonate units. Additionally, the methods are short, simple, efficient and utilize inexpensive starting materials. The present invention can also produce such compounds at relatively low cost.

More particularly, according to one embodiment of the present invention, a method for the preparation of thiophosphite esters having the formula

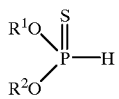

(1)

is disclosed, wherein $R^1$ and $R^2$, when present as substituents, are each independently substituted or unsubstituted alkyl, alkenyl, alkynyl, or aryl.

The method comprises the steps of (a) forming a reaction mixture of a phosphite having the formula

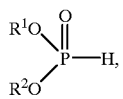

(2)

an effective amount of phosphorus pentasulfide and a suitable solvent, and (b) heating the reaction mixture at a suitable temperature until conversion of (2) to (1) is substantially complete.

Preferably, the alkyl, alkenyl or alkynyl is $C_{1-24}$ alkyl, alkenyl or alkynyl and the aryl is phenyl.

Typically, the suitable solvent is a nonpolar or polar aprotic solvent. Preferably, the nonpolar solvent is an aromatic solvent and is selected from the group consisting of benzene and toluene. When the suitable solvent is a polar aprotic solvent, preferably it is tetrahydrofuran.

Typically, the effective amount of phosphorus pentasulfide is between about 0.4–1.0:1.0 ($P_4S_{10}$:phosphite), preferably 0.5:1 ($P_4S_{10}$:phosphite).

According to one embodiment of the present invention, the solvent is benzene and a suitable temperature typically is between about 60° C. to about 95° C., preferably between about 70° C. to about 80° C.

According to another embodiment of the present invention, a method for the preparation of thiophosphonoformate esters having the formula

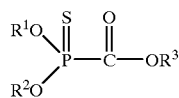

(3)

is disclosed, wherein $R^1$, $R^2$, and $R^3$, when present as substituents, are each independently substituted or unsubstituted alkyl, alkenyl, alkynyl or aryl.

The method comprises the steps of: (a) forming a reaction mixture of a thiophosphite ester having the formula

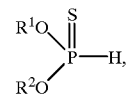

(1)

metallic sodium, $R^3$-chloroformate and a suitable solvent, wherein $R^1$, $R^2$, and $R^3$, when present as substituents, are each independently substituted or unsubstituted alkyl, alkenyl, alkynyl or aryl; and (b) warming the reaction mixture at a suitable temperature until formation of (3) is complete.

Preferably, the alkyl, alkenyl or alkynyl is $C_{1-24}$ alkyl, alkenyl or alkynyl and the aryl is phenyl.

In another preferred version of the present invention, $R_1$, $R_2$, or $R_3$ can be a protecting group masking an acidic function in (3). Suitable protecting groups include, but are not limited to, trimethylsilyl and benzyl.

In another preferred version of the present invention, $R_1$, $R_2$, or $R_3$ can be a protecting group, for the purpose of creating a pro-drug. A suitable protecting group can be removed from the pro-drug in vivo to give an active drug. Suitable protecting groups can include, but are not limited to the pivaloyloxymethyl (POM) group.

Typically, the suitable solvent is a nonpolar or polar aprotic solvent. Preferably, the nonpolar solvent is an aromatic solvent and is selected from the group consisting of benzene and toluene. When the suitable solvent is a polar aprotic solvent, preferably it is tetrahydrofuran.

According to one embodiment of the present invention, the suitable temperature typically is between about 40° C. to about 70° C., preferably between about 50° C. to about 60° C.

In yet another embodiment of the present invention, a method for the production of thiophosphonoformate esters having the formula

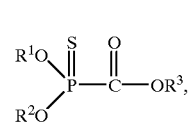

(3)

is disclosed, wherein $R^1$, $R^2$, and $R^3$, when present as substituents, are each independently substituted or unsubstituted alkyl, alkenyl, alkynyl or aryl or a suitable protecting group.

The method comprises the steps of: (a) forming a reaction mixture of a phosphonoformate ester having the formula

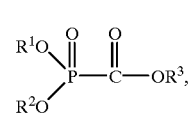

(4)

an effective amount of phosphorus pentasulfide and a suitable solvent, wherein $R^1$, $R^2$, and $R^3$, when present as substituents, are each independently substituted or unsubstituted alkyl, alkenyl, alkynyl or aryl or a suitable protecting group; and (b) heating said reaction mixture under a suitable temperature until conversion of (4) to (3) is substantially complete.

Preferably, the alkyl, alkenyl or alkynyl is selected from the group consisting of $C_{1-24}$ alkyl, alkenyl or alkynyl and the aryl is phenyl.

In another preferred version of the present invention, $R_1$, $R_2$, or $R_3$ can be a protecting group masking an acidic function in (3). Suitable protecting groups include, but are not limited to, trimethylsilyl and benzyl.

In another preferred version of the present invention, $R_1$ $R_2$, or $R_3$ can be a protecting group, for the purpose of creating a pro-drug. A suitable protecting group can be removed from the pro-drug in vivo to give an active drug. Suitable protecting groups can include, but are not limited to the pivaloyloxymethyl (POM) group.

Typically, the suitable solvent is a nonpolar or polar aprotic solvent. Preferably, the nonpolar solvent is an aromatic solvent and is selected from the group consisting of benzene and toluene. When the suitable solvent is a polar aprotic solvent, preferably it is tetrahydrofuran.

Typically, the effective amount of phosphorus pentasulfide is between about 0.4–1.0:1.0 ($P_4S_{10}$:phosphonoformate ester), preferably 0.5:1 ($P_4S_{10}$:phosphonoformate ester).

According to one embodiment of the present invention, the solvent is benzene and a suitable temperature typically is between about 60° C. to about 95° C., preferably between about 70° C. to about 80° C.

In still yet another embodiment of the present invention, the latter two methods can further comprise the step of separating (3) from said reaction mixture; and hydrolyzing (3) to form thiophosphonoformic acids and their additional salts.

These and other features, aspects, and advantages of the present invention will become better understood with reference to the following description and appended claims.

DESCRIPTION

According to one aspect of the present invention, there is provided improved methods for converting phosphite or phosphonate esters into corresponding thiophosphites or thiophosphonates and for synthesizing specific thiophosphite and thiophosphonate compounds. The methods start from phosphite diesters or phosphonate triesters using $P_4S_{10}$ (phosphorus pentasulfide) as the thionation reagent. The reaction mixture is refluxed at a suitable temperature until the reaction is complete. The sodium salt of the thiophosphite product may be used subsequently for phosphonylation of chloroformate esters to produce pure thiophosphonocarboxylate triesters. The method was used to prepare dimethyl thiophosphite and thence trimethyl thiophosphonoformate, a key intermediate in synthesis of salts of thiophosphonoformic acid, which have antiviral properties. Alternatively, thiophosphonoformate was prepared directly by the action of $P_4S_{10}$ on trimethyl phosponoformate.

Trimethyl thiophosphonate is a key intermediate in preparation of Thiovir®. However, this process involves conversion of trimethyl phosphonoformate into the corresponding thiono-derivative using Lawesson's Reagent as the thionation agent. The present invention teaches a two-step preparation of trimethyl thiophosphonoformate from dimethyl phosphite via dimethyl thiophosphite. Phosphorus pentasulfide is used as a thionation reagent to prepare the dimethyl thiophosphite from dimethyl phosphite. The dimethyl thiophosphite intermediate so prepared is converted to trimethyl thiophosphonoformate by reaction with methyl chloroformate. Thiovir® is then prepared by converting trimethyl thiophosphonoformate to tri sodium thiophosphonoformate as previously taught in the principal inventor's issued patents referred to above. This chemistry is of general utility for preparation of thiophosphite diesters and thiophosphonoformate triesters. Those skilled in the art will appreciate that the conversion of phosphite or phosphonoformate to their thio analogues can give an analogue of lower polarity, thus providing enhanced penetration of lipid membrane barriers. As a result, thionated phosphonoformate antiviral compounds of the present invention can have significantly higher oral bioavailability than the corresponding phosphonoformate compounds in treating cases of HIV infection and inhibiting HIV in general.

Another aspect of the present invention relies on the unexpected regioselectivity of $P_4S_{10}$ in thionation reactions. Thiophosphonate esters containing a carboxylate ester function have previously been obtained by selective thionation of corresponding phosphonate esters using Lawesson's Reagent (LR). In comparison, $P_4S_{10}$ is known to be a more reactive reagent than LR, and can even be used to prepare LR itself. Moreover, $P_4S_{10}$ is known in the art as an active and inexpensive thionation and deoxygenation reagent for converting C=O to C=S. Accordingly, it was completely unexpected that $P_4S_{10}$ would prove to be effective in converting carboxyphosphonate esters to thiophosphonocarboxylate esters, i.e., P=O to P=S in the presence of C=O, in accordance with the methods of the present invention.

The present invention discloses a general method for the thionation of phosphite and phosphonate esters utilizing $P_4S_{10}$ as the thionation reagent. Further, the present invention provides new, improved and uniquely effective procedures for rapidly, simply, and inexpensively producing large quantities of essentially pure thiophosphites and thiophosphonates. For example, these improved methods according to the present invention can produce large quantities of pure Thiovir® in a more cost effective manner. More importantly, the methods of the present invention make it possible to efficiently produce TPFA and other thio analogues in sufficient purity and quantity for use as new, effective antiviral agents against HIV and other viral pathogens.

According to one aspect of the present invention, there is provided a novel, improved process for the conversion of phosphites or phosphonates into corresponding thiophosphites or thiophosphonates in general, and specifically for production of trialkyl or triaryl thiophosphonoformate compounds by these procedures.

Trisodium phosphonoformate (foscarnet), a pyrophosphate analogue, is known to inhibit HIV reverse transcriptase with an $IC_{50}$ of about 1 $\mu$M and is also known to inhibit several Herpesvirus DNA polymerases, including the DNA polymerase of Cytomegalovirus (CMV). However, in clinical trials of PFA, reversible nephrotoxicity, characterized by increased serum creatinine or acute toxic tubolopathy, and also poor oral bioavailability, were reported [Gerard, L., et al. (1995), Pharmacology and clinical use of foscarnet, *International Journal of Antimicrobial Agents* 5(4) :209–217; and Noormohamed, F. H., et al. (1998), Pharmacokinetics and absolute bioavailability of oral foscarnet in human immunodeficiency virus-seropositive patients, *Antimcrobial Agents and Chemotherapy* 42(2); 293–297]. It would therefore be desirable to develop PFA analogues devoid of these shortcomings.

Preparations of trisodium thiophosphonoformate (Thiovir®) were previously claimed in DD 219198 by Issleib (herein incorporated by reference in its entirety including cited references), and the U.S. Pat. No. 5,072,032 by McKenna.

One version of the present invention is an improvement over the prior art methods, particularly in the regioselective introduction of a sulfur atom, wherein $P_4S_{10}$ replaces the much more expensive Lawesson's reagent in conversion of trimethyl PFA to trimethyl TPFA, which is then hydrolyzed to Na₃TPFA under specific alkaline conditions. According to the present invention, preparation of dimethyl thiophosphite via P₄S₁₀ can provide a facile route to the trimethyl TPFA intermediate. Further, according to the present invention, LR can be replaced by a much less expensive sulfur-transfer reagent, P₄S₁₀. Still further, the present invention provides the feasibility of introducing the sulfur atom at an earlier step (prior to formation of the C—P bond, using either LR or a less expensive alternative reagent, for example).

In general, the improved methods according to the present invention convert phosphite or phosphonate esters into corresponding thiophosphites or thiophosphonates. The methods start from phosphite diesters or phosphonate triesters and use P₄S₁₀ as the thionation reagent. The reaction mixture is heated until the reaction is complete and may be followed by separation and alkylation or arylation steps to produce pure thiophosphonocarboxylate triesters. The method can be used to prepare dimethyl thiophosphite and thence trimethyl thiophosphonoformate, a key intermediate in synthesis of salts of thiophosphonoformic acid, which have antiviral properties.

1. Methods of Making Thiophosphite and Thiophosphonate Compounds

The methods of the present invention provide novel, uniquely effective procedures for rapidly, simply, and inexpensively converting phosphite or phosphonate esters into corresponding thiophosphites or thiophosphonates and for synthesizing specific thiophosphite and thiophosphonate compounds.

A. Method of Synthesizing Thiophosphite Esters

More particularly, according to one embodiment of the present invention (see FIG. 1A), a method for the preparation of thiophosphite esters having the formula

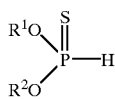

(1)

is disclosed, wherein $R^1$ and $R^2$ when present as substituents, are each independently substituted or unsubstituted alkyl, alkenyl, alkynyl or aryl.

The first step of this method is forming a reaction mixture of a phosphite having the formula

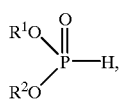

(2)

an effective amount of phosphorus pentasulfide and a suitable solvent.

Preferably, the alkyl, alkenyl, or alkynyl is $C_{1-24}$ alkyl, alkenyl, or alkynyl and the aryl is phenyl. Although compounds having lower alkyl, alkenyl, or alkynyl groups, e.g. $C_{1-4}$, may be readily obtained, end products having greater lipophilic properties, e.g. $C_5$–$C_{24}$ saturated or unsaturated aliphatic groups, may offer advantages with respect to oral bioavailability and cell permeability. Alternatively, $R_1$ or $R_2$ can be a suitable protecting group, for the purpose of creating a synthetic intermediate or pro-drug precursor. Suitable protecting groups are well known in the art. See, e.g. C. E. McKenna and J. Schmidhauser, J. C. S. Chem. Comm., 729 (1979); and T. W. Greene and P. G. M. Wuts, "Protective Groups in Organic Synthesis," 3rd ed., John Wiley, New York (1999), which are incorporated herein by reference.

The effective amount of phosphorus pentasulfide typically is between about 0.4–1.0:1.0 (P₄S₁₀:phosphite). Preferably, the effective amount of phosphorus pentasulfide is 0.5:1 (P₄S₁₀:phosphite).

B. Method of Synthesizing Thiophosphonoformate Esters from Thiophosphite Esters

According to another embodiment of the present invention (see FIG. 1A), a method for the preparation of thiophosphonoformate esters having the formula

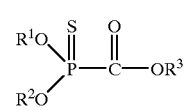

(3)

is disclosed, wherein $R^1$, $R^2$ and $R^3$, when present as substituents, are each independently substituted or unsubstituted alkyl, alkenyl, alkynyl or aryl.

Preferably, the alkyl, alkenyl or alkynyl is $C_{1-24}$ alkyl, alkenyl, or alkynyl and the aryl is phenyl. Although lower alkyl, alkenyl, or alkynyl groups may be readily obtained, end products having greater lipophilic properties, e.g. $C_5$–$C_{24}$ saturated or unsaturated aliphatic groups, may offer advantages with respect to oral bioavailability and cell permeability.

In another preferred version of the present invention, $R_1$, $R_2$, or $R_3$ can be a protecting group masking an acidic function in (3). Suitable protecting groups include, but are not limited to, trimethylsilyl and benzyl.

In another preferred version of the present invention, $R_1$ $R_2$, or $R_3$ can be a protecting group, for the purpose of creating a pro-drug. A suitable protecting group can be removed from the pro-drug in vivo to give an active drug. Suitable protecting groups can include, but are not limited to the pivaloyloxymethyl (POM) group.

The first step of this method is forming a reaction mixture of a thiophosphite ester having the formula

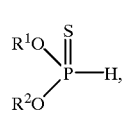

(1)

metallic sodium, $R^3$-chloroformate and a suitable solvent, wherein $R^1$, $R^2$ and $R^3$, when present as substituents, are each independently substituted or unsubstituted alkyl, alkenyl, alkynyl or aryl. Preferably, the alkyl, alkenyl or alkynyl is $C_{1-24}$ alkyl, alkenyl, or alkynyl and the aryl is phenyl.

In another preferred version of the present invention, $R_1$, $R_2$, or $R_3$ can be a protecting group masking an acidic function in (3). Suitable protecting groups include, but are not limited to, trimethylsilyl and benzyl.

In another preferred version of the present invention, $R_1$ $R_2$, or $R_3$ can be a protecting group, for the purpose of creating a pro-drug. A suitable protecting group can be removed from the pro-drug in vivo to give an active drug. Suitable protecting groups can include, but are not limited to the pivaloyloxymethyl (POM) group.

Typically, the suitable solvent is a nonpolar or polar aprotic solvent. Exemplary nonpolar solvents are aromatic solvents such as benzene or toluene, though those skilled in the art will appreciate that any suitable nonpolar solvent can be used. When the suitable solvent is an aprotic solvent, preferably it is tetrahydrofuran.

Following the formation of the reaction mixture, the mixture is warmed under a suitable temperature until formation of (1) is substantially complete. Preferably, the warming will take place under an inert anhydrous atmosphere to prevent interference with the conversion reaction. Exemplary heating temperatures can range from approximately 40° C. to about 70° C. depending on the solvent utilized and may include reflux conditions. Additionally, heating times may be 1 hour or more, preferably on the order of about 1 to 2 hours. Preferably, heating temperatures can range from approximately 50° C. to about 60° C.

Figure 1B:
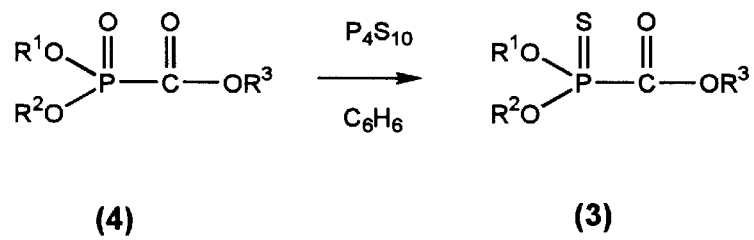
FIG. 1B schematically shows thionation by $P_4S_{10}$ of a phosphonoformate triester (4) to give a thiophosphonoformate triester (3)

C. Method of Synthesizing Thiophosphonoformate Esters from Phosphonoformate Esters In yet another embodiment of the present invention (see FIG. 1B), a method for the production of thiophosphonoformate esters having the formula

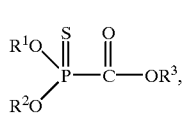

(3)

is disclosed, wherein $R^1$, $R^2$, and $R^3$, when present as substituents, are selected from the group consisting of substituted or unsubstituted alkyl, alkenyl, alkynyl, and aryl. Alternatively, $R_1$, $R_2$, or $R_3$ can be a suitable protecting group.

The first step of the method comprises forming a reaction mixture of a phosphonoformate ester having the formula

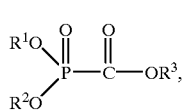

(4)

an effective amount of phosphorus pentasulfide and a suitable solvent, wherein $R^1$, $R^2$, and $R^3$, when present as substituents, are each independently substituted or unsubstituted alkyl, alkenyl, alkynyl or aryl Preferably, the alkyl, alkenyl or alkynyl is selected from the group consisting of $C_{1-24}$alkyl, alkenyl or alkynyl and the aryl is phenyl. Although compounds having lower alkyl, alkenyl, or alkynyl groups, e.g., $C_{1-4}$, may be readily obtained, end products having greater lipophilic properties, e.g.$C_5-C_{24}$ saturated or unsaturated aliphatic groups, may offer advantages with respect to oral bioavailability and cell permeability.

In another preferred version of the present invention, $R_1$, $R_2$, or $R_3$ can be a protecting group masking an acidic function in (3). Suitable protecting groups include, but are not limited to, trimethylsilyl and benzyl.

In another preferred version of the present invention, $R_1$ $R_2$, or $R_3$ can be a protecting group, for the purpose of creating a pro-drug. A suitable protecting group can be removed from the pro-drug in vivo to give an active drug. Suitable protecting groups can include, but are not limited to the pivaloyloxymethyl (POM) group.

The effective amount of phosphorus pentasulfide typically is between about 0.4–1.0:1.0 ($P_4S_{10}$:phosponoformate ester). Preferably, the effective amount of phosphorus pentasulfide is 0.5:1 ($P_4S_{10}$:phosphonoformate ester).

Typically, the suitable solvent is a nonpolar or aprotic solvent. Exemplary nonpolar solvents are aromatic solvents such as benzene or toluene, though those skilled in the art will appreciate that any suitable nonpolar solvent can be used. When the suitable solvent is an aprotic solvent, preferably it is tetrahydrofuran.

Following the formation of the reaction mixture, the mixture is heated at a suitable temperature until conversion of (4) to (3) is substantially complete. Preferably, the heating will take place under an inert anhydrous atmosphere to prevent interference with the conversion reaction. Exemplary heating temperatures can range from approximately 60° C. to about 95° C. depending on the solvent utilized and may include reflux conditions. Additionally, heating times may be 1 hour or more, preferably on the order of about 1 to 2 hours. Preferred heating temperatures can range from approximately 70° C. to about 80° C. when the solvent is benzene.

Lawesson's reagent can be used in place of $P_4S_{10}$ for preparation of thiophosphonate esters, however, the former reagent is significantly more expensive than the latter one.

D. Following the Completion of the Aforementioned Reactions p In still yet another embodiment of the present invention, the latter two methods can further comprise the step of separating (3) from said reaction mixture; and hydrolyzing (3) to form thiophosphonoformic acids and their additional salts. Of equal or greater significance, the methods of the present invention make it possible to efficiently produce Thiovir® and its derivatives in sufficient purity for a variety of uses known to those skilled in the art. Once the aforementioned esters are made, the methods can further include steps such as separating the esters from said reaction mixture and hydrolyzing the esters to yield the respective thiophosphonoformic acids and their additional salts. Separation of the esters from the reaction mixture can be accomplished if desired through distillation or any method known to those skilled in the art. For example, the solvent can be evaporated and any side product can be precipitated out of the solution. Conversely, distillation can be used to distill the thio analogues from the mixture directly. Using the foregoing methodology, and distilling the product directly from the reaction mixture can produce relatively pure products with substantially high yields. Further, the esters can be further modified through hydrolysis to produce the corresponding thiophosphonoformic acid (TPFA) and its salts. Preferably, when desired, hydrolysis will take place under basic conditions such as the utilization of sodium hydroxide (NaOH) to directly hydrolyze thiophosphonate esters to their corresponding acids. However, those skilled in the art will appreciate that other hydrolysis methods, including the correct usage of ITMS are contemplated as being within the scope of the present invention and that hydrolysis of the esters can be accomplished by any one of a number of methods known to those skilled in the art. Though ITMS-$H_2O$ (buffered to near neutral to alkaline pH) may not hydrolyze the ethyl ester of Thiovir® effectively, it can hydrolyze the methyl ester.

Solvents other than tetrahydrofuran, benzene and toluene can be utilized as well as other inert gases in place of the argon disclosed and claimed. Additionally, other phosphonate starting materials may be utilized than those disclosed in the following non-limited examples.

In general, ethyl esters of phosphorus derivatives can be significantly more stable than the methyl esters and the products of methyl esters can often be more difficult to purify.

Although the above-mentioned thionation processes with $P_4S_{10}$ have addressed converting phosphite and phosphonoformate esters to their corresponding analogues, the present invention is not limited to those examples. Other phosphorus derivatives can be thionated via $P_4S_{10}$. These derivatives can include and not be limited to esters of methylenebisphosphonic acid, phosphonoacetic acid (PAA), their functional derivatives and analogues. Functional derivatives and analogues can include but not be limited to esters, salts, and halogenated derivatives.

Since the reagents utilized for these essentially one-step reactions are relatively inexpensive compared to previous methods, and the yields of pure product are high, the economies of the present invention are readily apparent.

II. Further Optimization of Reaction Parameters

Figure 2:
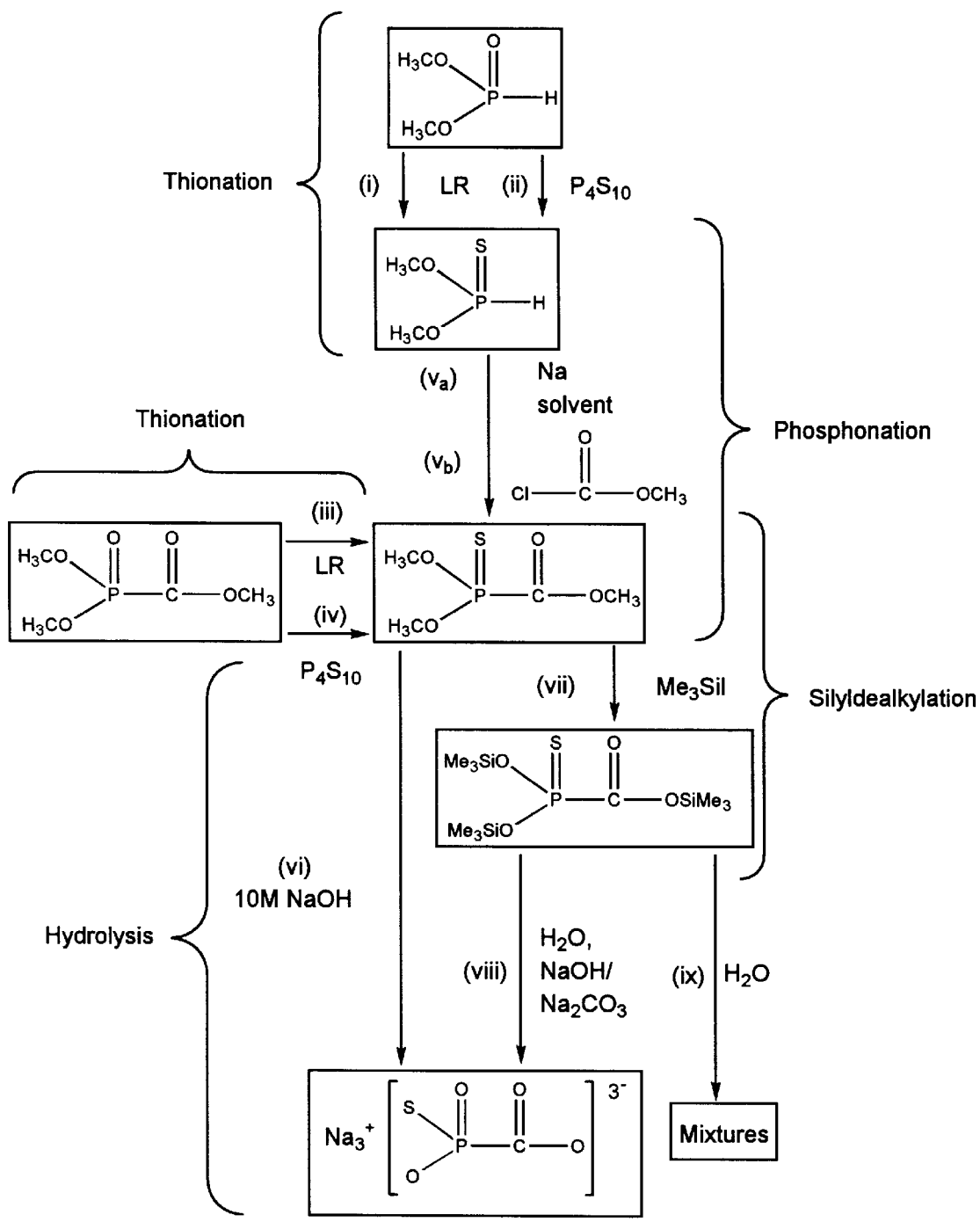
FIG. 2 schematically shows the following: (i), (ii), (iv), and (v) comprise the improved methods of producing thiosphosphite and thiophosphonoformate compounds; (iii)+(vi) are methods from U.S. Pat. No. 5,072,032; (vii)+(ix) are related to a claimed literature process, which we reinvestigated; and (viii) is an improvement of (ix) to produce TPFA trisodium salt.

Referring to FIG. 2, the first new route explored begins from the inexpensive starting material, dimethyl phosphite. This compound can be readily thionated by LR in refluxing benzene [route (i) in FIG. 2], the product being obtained in 86% distilled yield. NMR $^1H$: $\delta$ 7.69 (d, 1H, $^1J_{HP}$=651 Hz); 3.73 (m, 6H, $^3J_{HP}$=12 Hz); $^{13}C$: $\delta$ 52.4 (d, $^2J_{CP}$=7 Hz, $CH_3$); $^{31}P$: $\delta$ 74.8 (d, $^1J_{PH}$=652 Hz, $^3J_{PH}$=14.6 Hz). According to the $^1H$ and $^{31}P$ chemical shift ($\delta$) data and $^1J_{HP}$ and $^1J_{PH}$ values, the structure of the thioproduct was unequivocally identified as dimethyl thiophosphite (1).

According to one aspect of the present invention, replacing LR by $P_4S_{10}$ [Route (ii) in FIG. 2] gives only a slightly lower yield of distilled dimethyl thiophosphite. The thiophosphite diester product from either thionation reaction then reacts smoothly (as its Na salt) with methyl chloroformate to give trimethyl thiophosphonoformate (3) in over 60% distilled yield. NMR: $^1H$: $\delta$ 3.85 (d, 6H, $^3J_{HP}$=4 Hz, $POCH_3$); 3.88 (s, 3H, $COCH_3$); $^{13}C$: $\delta$166.5 (d, $^1J_{CP}$=225 Hz, $CO$), 54.5 (d, $^2J_{CP}$=5 Hz, $POCH_3$), 52.9 (s, $COCH_3$); $^{31}P\{H\}$: $\delta$ 64.9 (s); HRMS: Calcd for $C_4H_9O_4PS$ 183.9959, Found=183.9959.

Introduction of S prior to C—P bond formation using LR as the thionation reagent [route (i) in FIG. 2] reduces the cost of the intermediate (a component of this savings is avoidance of the expense of purchasing pre-synthesized trimethyl PFA versus dimethyl phosphite, at the cost of introducing an extra step into the synthesis). However, replacement of LR by $P_4S_{10}$ can also result in a reduction in the cost. Further, the reaction using $P_4S_{10}$ proceeded well, using benzene as solvent in place of the more costly acetonitrile.

$P_4S_{10}$ can also be used as a substitute for LR using trimethyl PFA as the substrate to be thionated. $P_4S_{10}$ again gave a slightly lower yield than LR, but regioselectivity (P=O vs. C=O selectivity) was good (product distilled and analyzed by $^1H$, $^{13}C$ and $^{31}P$ NMR). The cost of the process is significantly lowered by substituting $P_4S_{10}$ for LR.

| Method | Thionation Time | Temperature | Phosphonation Time | Temperature | Reaction Conditions Applied Solvent | Protection Gas |
|---|---|---|---|---|---|---|
| (i) + (v) | 1 hr | 80° C. | 2 hr | 60° C. | Benzene | $N_2$ |
| (ii) + (v) | 2.5 hr | 80° C. | 2 hr | 60° C. | Benzene | $N_2$ |
| (iii) | 5 hr | 80° C. | | | Acetonitrile | Ar |
| (iv) | 2.5 hr | 80° C. | | | Benzene | $N_2$ |

Several of the starting materials and intermediates are sensitive to oxygen and humidity. Accordingly, the reactions were performed under an inert atmosphere ($N_2$ or Ar).

With respect to the conversion to $Na_3TPFA$, an ITMS silyldealkylation procedure was used with alkaline rather than unbuffered aqueous hydrolysis of the silylated intermediate to lessen formation of side products and to minimize decomposition. Changing the intermediate from the ethyl to the methyl ester is also an important modification making this approach more praticable. Alternatively, by adjusting the hydrolysis conditions, using NaOH in methanol, the product yields can be improved from about 27% to at least 35%.

The following Examples below illustrate several important embodiments of the method according to the present invention.

EXAMPLES

I. General Experimental Protocol

All reactions in these Examples were performed in scrupulously oven- or flame-dried glassware under $N_2$. All reactions were performed under dry, pre-purified $N_2$ or argon (passed successively through columns of drierite; activated Linde Type 4A molecular sieves; and BASF catalyst). Lawesson's reagent was purchased from Aldrich Chemical Company (97%) and was used without further purification. Trimethyl phosphonoformate, (purified by vacuum distillation prior to use, 60° C., 0.015 mm), $P_4S_{10}$, diethyl phosphite and diphenyl phosphite were also purchased from Aldrich Chemical Company.

All solvents and other reagents were of reagent grade quality, purchased commercially, and used without further purification, except as noted below. Neutral silica gel (60 Å) was used for column chromatography. Tetrahydrofuran was distilled from benzophenone/sodium ketal, then from lithium aluminum hydride; benzene and toluene were distilled from $CaH_2$.

NMR spectra were recorded on a Bruker AM 360 spectrometer. $^1H$ and $^{13}C$ NMR chemical shifts are referenced to external tetramethylsilane and benzene. $^{31}P$ NMR chemical shifts are referenced to external 85% $H_3PO_4$. UV spectra were recorded on a Shimadzu UV-260 spectrophotometer. Infrared (IR) spectra were recorded on a Perkin-Elmer 281 spectrometer. Melting points were recorded on a Thomas Hoover apparatus. Vacuum distillations were performed on a vacuum line equipped with an all glass oil diffusion pump; pressures were measured on a MacLeod gauge. High resolution mass spectra were obtained at the Mass Spectral Facility, University of California, Riverside, Calif. Elemental analysis were performed by Galbraith Laboratories, Knoxville, Tenn.

II. Synthesis of Thiophosphite Diesters

A. Synthesis of Dimethyl Thiophosphite using LR as Thionation Agent:

Dry benzene (400 ml) and LR (40 g, 0.1 mole) were charged into a 1,000 mL three-necked round-bottom flask. Dimethyl phosphite (21.6 g, 0.19 mole, 18 mL) was added under $N_2$ with stirring, and the reaction mixture was heated to reflux until the $^{31}P$-NMR peak of dimethyl phosphite disappeared (1 hr.). The mixture was evaporated, and the residue was distilled in vacuo: oily liquid, 21.3 g (b.p. 49–50° C./6 mm Hg) (85.5%). NMR $^1H$: $\delta$ 7.69 (d, 1H, $^1J_{HP}$=651 Hz); 3.73 (m, 6H, $^3J_{HP}$=12 Hz); $^{13}C$: $\delta$ 52.4 (d, $^2J_{CP}$=7 Hz, $CH_3$); $^{31}P$: $\delta$ 74.8 (d, $^1J_{PH}$=652 Hz, $^3J_{PH}$=15 Hz).

B. Synthesis of Diethyl Thiophosphite using LR as Thionation Agent:

Dry benzene (120 mL) and LR (26 g, 0.06 mole) were charged into a 500 mL three-necked round-bottom flask. Diethyl phosphite (16 g, 0.116 mole) was added under $N_2$ with stirring, and the reaction mixture was heated to reflux for 2 hr. The reaction mixture was evaporated. The residue was distilled in vacuo: oily liquid, 1 hg (b.p. 32–34° C./0.02 mm Hg) (61.5%) NMR: $^1$H: δ 7.70 (d, 1H, $^1J_{PH}$=648 Hz), 4.08–4.16 (m, 4H) 1.31 (t, 6H, $^3J_{HH}$=7 Hz); $^{13}$C: δ 62.2 (CH$_2$), 16.1 (CH$_3$); $^{31}$P {H}: δ 69.9.

C. Synthesis of Dimethyl Thiophosphite using P$_4$S$_{10}$ as Thionation Agent:

P$_4$S$_{10}$ (11 g, 0.025 mole) was suspended in dried benzene (60 mL). Dimethyl phosphite (5.5 g, 0.05 mole, 4.6 mL) was added. The reaction mixture was refluxed under N$_2$ until the ratio by $^{31}$P-NMR was 80:20 (thiophosphite: phosphite) (1.5 hr). The product was filtered and distilled in vacuo: oil, 4.5 g (b.p. 49–50° C./6 mm Hg) (71%). NMR $^1$H: δ 7.68 (d, 1H, $^1J_{HP}$=652 Hz, PH), 3.71–3.77 (m, 6H, $^3J_{HP}$=14 Hz, CH$_3$); $^{13}$C: δ 52.3 (d, $^2J_{CP}$=7 Hz, CH$_3$); $^{31}$P {H}: 74.8, $^{31}$P: δ 74.8 (dxq, $^1J_{PH}$=652 Hz, $^1J_{PH}$=14 Hz).

D. Synthesis of Diethyl Thiophosphite using P$_4$S$_{10}$ as Thionation Agent:

P$_4$S$_{10}$ (11 g, 25 mmole) was suspended in dried toluene (120 mL). Diethyl phosphite (6.9 g, 50 mmole) was added. The reaction mixture was refluxed under N$_2$ until the product ratio by $^{31}$P-NMR was 80:20 (thiophosphite:phosphite) (1.5 hr). The reaction mixture was filtered and distilled in vacuo: oil, 6.2 g (b.p. 30–32° C./0.02 mm Hg) (80.5%). NMR $^1$H: δ 7.70 (d, 1H, $^1J_{HP}$=648 Hz), 4.08–4.16 (m, 4H), 1.31 (t, 6H, $^3J_{HH}$=7 Hz); $^{13}$C: δ 62.2 (CH$_2$), 16.1 (CH$_3$); $^{31}$P {H}: δ 69.8, $^{31}$P: δ 69.8 (dxm, $^1J_{PH}$=647 Hz).

E. Synthesis of Dipropyl Thiophosphite using P$_4$S$_{10}$ as Thionation Agent:

P$_4$S$_{10}$ (3.4 g, 8 mmole) was suspended in dried benzene (40 mL). Dipropyl phosphite (2.5 g, 16 mmole 2.45 mL) was added. The reaction mixture was refluxed under N$_2$ until the product ratio by $^{31}$P-NMR was 80:20 (thiophosphite: phosphite) (2.5 hr). The reaction mixture was filtered and distilled in vacuo: oil, 2.04 g (b.p. 44–45° C./0.05 mm Hg) (75%). NMR: $^1$H: δ 7.74 (d, 1H, $^1J_{HP}$=648 Hz), 4.0–4.06 (m, 4H), 1.66–1.70 (m, 4H), 0.93–0.99 (m, 6H); $^{13}$C: δ 62.2, 32.3 (CH$_2$), 16.1 (CH$_3$); $^{31}$P{$^1$H}: δ 70.0, $^{31}$P δ 70.0 (dxm, $^1J_{PH}$=648 Hz). HRMS: (EI) calcd for C$_6$H$_{15}$O$_2$PS: 182.0530; found: 182.0530.

F. Synthesis of Diphenyl Thiophosphite using P$_4$S$_{10}$ as Thionation Agent:

Diphenyl phosphite (1.2 g, 5 mmole) was added to P$_4$S$_{10}$ (0.44 g, 1 mmole). The reaction mixture was stirred and heated to 90° C. under N$_2$, for 2 hr. After the reaction cooled to room temperature, 100 mL of water was added and the aq. solution was extracted with CHCl$_3$ (3×50 mL). The oil layer was dried over anh. MgSO$_4$ and evaporated. The residue was partly purified with chromatography through silica gel (CH$_2$Cl$_2$ as eluting agent); 0.6 g of product was obtained. According to $^{31}$P{$^1$H} NMR analysis, this product included a side product (20%). NMR: $^1$H: δ 8.3 (d, $^1J_{HP}$=668 Hz), 7.4–7.2 (m, phenyl H) (thiophosphite); $^{13}$C: δ 129.9, 125.8, 125.7, 121.3 (thiophosphite), 129.7, 125.7, 121.2, 121.1 (side product); $^{31}$P{$^1$H}: δ 64.8 (thiophosphite), 53.7 (side product); after flash column chromatography eluted with CH$_2$Cl$_2$, 0.4 g pure product was collected. $^1$H:δ 8.3 (d, 1H, $^1J_{MP}$=668 Hz, 7.4–7.2 (m, 10H, phenyl); $^{13}$C: δ 129.9, 125.8, 125.7, 121.3; $^{31}$P: δ 64.9 (d, $^1J_{PH}$=668 Hz), 53.7(s); HRMS: (EI) calcd for C$_{12}$H$_{11}$O$_2$PS: 250.0217; found: 250.0218.

III. Synthesis of Thiophosphonoformic Acid Triesters

A. Synthesis of Trimethyl Thiophosphonoformate:

Metallic sodium (0.55 g, 0.024 mole) was suspended in THF (20 mL), dimethyl thiophosphite (3 g, 0.024 mole) was added, and warmed at 60° C. (oil bath) for 2 hr under N$_2$, until the $^{31}$P-NMR peak of the starting material disappeared. The mixture was cooled to room temperature. Methyl chloroformate (1.5 g, 0.024 mole, 1.26 mL) was added dropwise. After addition, the mixture was warmed to 60° C. (oil bath) for 2 hr. cooled to room temperature and allowed to stand overnight. Water (10 mL) and benzene (10 mL) were added, the layers were separated, and the oil and aqueous layers were washed with water and benzene respectively. The combined organic phases were dried with MgSO$_4$. After concentration, the residue was distilled in vacuo: oil, 2.72 g (b.p. 54–56° C./20 μ) (60%). NMR: $^1$H: δ 3.85 (d, 6H, $^3J_{HP}$=4 Hz, POCH$_3$) 3.88 (s, 3H, COCH$_3$); $^{13}$C: δ 166.5 (d, $^1J_{CP}$=225 Hz, CO), 54.5 (d, $^2J_{CP}$=5 Hz, POCH$_3$), 52.9 (s, COCH$_3$); $^{31}$P{$^1$H}: δ 64.9 (s); HRMS: found for C$_4$H$_9$O$_4$PS: 183.9959; calcd: 183.9959.

B. Synthesis of Triethyl Thiophosphonoformate:

Metallic sodium (0.9 g, 39 mmole) was suspended in benzene (60 mL) and diethyl thiophosphite (6 g, 39 mmole) was added and warmed at 60° C. (oil bath) for 5 hr under N$_2$, until the $^{31}$P-NMR peak of the starting material disappeared. The mixture was cooled to room temperature. Ethyl chloroformate (4.4 g, 39 mmole) was added dropwise. After addition, the mixture was warmed to 60° C. (oil bath) for 7 hr, cooled to room temperature and allowed to stand overnight. Water (20 mL) was added, the layer was separated, and the oil and aqueous layers were washed with water and benzene respectively. The combined organic phases were dried over MgSO$_4$. After concentration, the residue was distilled in vacuo: oil, 4.59 g (b.p. 68–70° C./20 μ) (61%). NMR: $^1$H: δ 4.21 (m, 6H, $^3J_{HP}$=4 Hz, CH$_2$) 1.27 (m, 9H, CH$_3$); $^{13}$C: δ 167.3, (d, $^1J_{CP}$=225 Hz, CO), 64.3 [P(S)OCH2], 62.1 (COOCH$_2$), 15.9 [P(S)OCH$_2$CH$_3$] 13.8 [C(O)OCH$_2$CH$_3$]; $^{31}$P {$^1$H}: δ 58.6 (s). Microanalysis calcd for C$_7$H$_{15}$O$_4$PS, C: 37.16, H: 6.68, S: 14.47; found, C: 36.71, H: 6.64; S: 14.48.

C. Preparation of Trimethyl Thiophosphonoformate from Trimethyl Phosphonoformate using P$_4$S$_{10}$ as Thionation Agent:

P$_4$S$_{10}$ (15 g, 0.03 mole) was suspended in dry benzene (60 mL), and trimethyl PFA (8.4 g, 0.05 mole) was added. The reaction mixture was refluxed for 2.5 hr (phosphonate peak disappeared by $^{31}$P-NMR). The product was filtered, concentrated, and extracted with 20 mL×3 portions of hexane. The combined extracts were dried over anhydrous Na$_2$SO$_4$, and the solvent evaporated; distillation in vacuo gave 7.30 g (80%) of product: b.p. 54–56° C./20 μ. NMR: $^1$H: δ 3.89 (s, 3H, COCH$_3$), 3.85 (m, 6H, POCH$_3$); $^{13}$C: δ 167.5 (d, $^1J_{CP}$=227 Hz, CO), 54.5 (d, $^{2J}_{CP}$=6 Hz, POCH$_3$), 52.9 (s, COCH$_3$); $^{31}$P {$^1$H}: δ 64.9.

The previously described present invention has a number of advantages. The advantages include the discovery of improved methods for synthesis of thiophosphites and thiophosphonoformate intermediates and a novel synthesis of Thiovir® and derivatives in a simple, fast, efficient manner with high yields. The versatility and the useful potential applications of these derivatives, makes these compounds especially valuable.

Although the present invention has been described in considerable detail with reference to certain preferred versions, other versions are possible. Thus, the spirit and scope of the appended claims should not be limited to the description of the preferred versions contained herein.

What is claimed is:

1. A method for the preparation of thiophosphite esters having the formula the method comprising the steps of:

(a) forming a reaction mixture of a phosphite having the formula

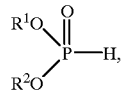

and an amount of tetraphosphorus decasulfide ($P_4S_{10}$) sufficient for thionation of the phosphite, wherein $R^1$ and $R^2$ are substituted or unsubstituted alkyl, alkenyl, alkynyl, or aryl or a suitable protecting group; and (b) heating the reaction mixture at a suitable temperature, which induces the thionation reaction, until conversion of the phosphite (2) to the thiophosphite ester (1) is substantially complete.

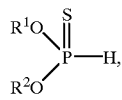

2. The method of claim 1, wherein the alkyl, alkenyl, or alkenyl is $C_{1-24}$ alkyl, alkenyl or alkynyl; the aryl is phenyl; and the suitable protecting group is trimethylsilyl, benzyl, or pivaloyloxymethyl.

3. The method of claim 1, wherein the reaction mixture includes a nonpolar or polar aprotic solvent.

4. The method of claim 3, wherein the nonpolar solvent is an aromatic solvent.

5. The method of claim 4, wherein the aromatic solvent is selected from the group consisting of benzene and toluene.

6. The method of claim 3, wherein the polar aprotic solvent is tetrahydrofuran.

7. The method of claim 1, wherein the amount of tetraphosphorus decasulfide is between about 0.2–1.0:1.0 ($P_4S_{10}$:phosphite).

8. The method of claim 7, wherein the amount of tetraphosphorus decasulfide is about 0.5:1 ($P_4S_{10}$:phosphite).

9. The method of claim 1, wherein the suitable temperature is between about 60° C. to about 95° C.

10. The method of claim 9, wherein the suitable temperature is between about 70° C. to about 80° C.

* * * * *